United States Patent [19]

Kellen et al.

[11] Patent Number: 4,847,137
[45] Date of Patent: Jul. 11, 1989

[54] PRESSURE-SENSITIVE ADHESIVE CROSSLINKED BY COPOLYMERIZABLE AROMATIC KETONE MONOMERS

[75] Inventors: James N. Kellen, Oakdale; Charles W. Taylor, Lake Elmo, both of Minn.

[73] Assignee: Minnesota Mining and Manufacturing Company, St. Paul, Minn.

[21] Appl. No.: 146,033

[22] Filed: Jan. 19, 1988

Related U.S. Application Data

[62] Division of Ser. No. 864,825, May 19, 1986, Pat. No. 4,737,559.

[51] Int. Cl.$^4$ .................. B05D 3/08; B05D 3/02; B05D 5/10
[52] U.S. Cl. .................... 428/195; 428/522; 156/275.7; 156/275.5; 156/327; 427/54.1; 427/208.4
[58] Field of Search .............. 428/424.2, 475.8, 483, 428/500, 195, 522; 427/54.1, 208.4; 156/275.5, 275.7, 327

[56] References Cited

U.S. PATENT DOCUMENTS

| | | | |
|---|---|---|---|
| Re. 24,906 | 12/1960 | Ulrich | 526/328.5 |
| 2,884,126 | 4/1959 | Ulrich | 428/355 |
| 2,956,904 | 10/1960 | Hendricks | 428/345 |
| 3,006,895 | 10/1961 | Sovish | 526/316 |
| 3,121,021 | 2/1964 | Copeland | 427/230 |
| 3,321,451 | 5/1967 | Gander | 526/287 |
| 3,475,363 | 10/1969 | Gander | 523/111 |
| 3,532,652 | 10/1976 | Zang | 428/355 |
| 3,998,997 | 12/1976 | Mowdood et al. | 526/271 |
| 4,140,115 | 2/1979 | Schonfeld | 128/156 |
| 4,165,266 | 8/1979 | Stueben et al. | 204/159 |
| 4,181,752 | 1/1980 | Martens et al. | 427/54 |
| 4,260,659 | 4/1981 | Gobran | 428/217 |
| 4,374,883 | 2/1983 | Winslow | 428/40 |
| 4,551,388 | 11/1985 | Schlademan | 428/355 |
| 4,554,324 | 11/1985 | Husman et al. | 525/301 |
| 4,693,776 | 9/1987 | Krampe et al. | 156/327 |

FOREIGN PATENT DOCUMENTS

| | | |
|---|---|---|
| 2443414 | 3/1976 | Fed. Rep. of Germany . |
| 2743979 | 4/1979 | Fed. Rep. of Germany . |

OTHER PUBLICATIONS

Toshio Okada, "Radiation Curing of Pressure-Sensitive Adhesives," a Japanese language publication published in the Journal of the Japanese Adhesion Society, vol. 20, No. 6, pp. 256–267, 1984; and accompanying English translation of this reference.

*Primary Examiner*—Joseph L. Schofer
*Assistant Examiner*—Peter F. Kulkosky
*Attorney, Agent, or Firm*—Donald M. Sell; Walter N. Kirn; Dale E. Hulse

[57] ABSTRACT

A pressure-sensitive adhesive is provided which is a copolymer of an acrylate monomer which contributes to the visco-elastic properties of the copolymer and a copolymerizable mono-ethylenically unsaturated aromatic ketone comonomer free of ortho-aromatic hydroxyl groups by means of which the copolymer can be crosslinked upon exposure to ultraviolet radiation such that the amount of crosslinking comonomer and the degree of polymerization of the copolymer are controlled to obtain a creep compliance value of at least about $1.2 \times 10^{-5}$ cm$^2$/dyne, the adhesive exhibits an enhanced level of initial adhesion when applied to skin but resists objectionable adhesion build-up over time. A preferred crosslinking ethylenically unsaturated hydroxyl-free aromatic ketone comonomer is p-acryloxybenzophenone.

20 Claims, 3 Drawing Sheets

PRESSURE-SENSITIVE ADHESIVE CROSSLINKED BY COPOLYMERIZABLE AROMATIC KETONE MONOMERS

This application is a division of U.S. application Ser. No. 864,825, filed May 19, 1986, now U.S. Pat. No. 4,737,559.

FIELD OF THE INVENTION

The invention relates to a crosslinked pressure-sensitive adhesive composition and to a tape utilizing such an adhesive.

BACKGROUND OF THE INVENTION

For more than half a century, pressure-sensitive adhesive (PSA) tapes have been used as packaging means for holding, sealing, protecting and as masking tapes in painting operations. The use of radiant energy to improve the physical properties of PSAs and, particularly, of PSA coatings, can be found as early as 1960 in U.S. Pat. No. 2,956,904 (Hendricks) wherein the use of high energy electron beam radiation is disclosed to increase the cohesive strength of the PSA coating.

U.S. Pat. No. 4,181,752 (Martens et al) teaches the in situ polymerization of acrylic monomer and comonomer syrups subjected to ultraviolet radiation at a very precise intensity of exposure of 0.1 to 7 milliwatts per $cm^2$ which optimizes the molecular weight of the resulting polymer. The photoinitiator selection is not as critical as the rate of ultraviolet dosage. Crosslinking of the adhesive by use of photoactive crosslinkers is disclosed; various benzophenone-type compounds are among the photoactive crosslinkers that are disclosed.

U.S. Pat. No. 4,165,260 (Stueben et.al.) discloses compositions comprising a poly(vinyl alkyl ether), a liquid monoacrylate monomer and a photoinitiator which compositions cure upon exposure to radiation to form a pressure-sensitive adhesive. Benzophenone is disclosed as the preferred photoinitiator.

Copolymerizable aromatic ketone monomers have been incorporated into pressure-sensitive adhesive copolymers. U.S. Pat. No. 3,998,997 discloses the use of copolymerizable hydroxy-aromatic ketone monomers at a level of at least 1% or an aromatic ketone monomer free of aromatic hydroxyl groups, e.g., diacetophenone acrylamides, at a level of two percent by weight, to improve the shear strength of an acrylate-functional pressure-sensitive adhesive. The patent discloses the use of multi-ethylenically unsaturated compounds as crosslinking agents, but does not address the compliance of the adhesive and does not disclose the use of ultra-violet radiation in preparing the disclosed adhesive.

A review article entitled "Radiation Curing of Pressure-Sensitive Adhesives, authored by Toshio Okada, published in the journal (Japanese language publication identified by Exhibit A of Applicants Information Disclosure Statement filed herewith) Vol. 20, No. 611984, discloses that copolymers of benzoin acrylate and an acrylate monomer such as 2-ethylhexylacryalte can be cured upon exposure to ultraviolet radiation to yield a pressure-sensitive adhesive having solvent-resistance environmental resistance and heat resistance (above 200° C.). It is believed that the degree of crosslinking of an adhesive having such properties would result in an adhesive having a very low degree of compliance.

The difficulty of adhering tape or other devices to the human skin has long been recognized. The irregular and complex surface of the skin presents obstacles in itself and the wide variation in the skin surface from individual to individual and from site to site on the same individual compound these obstacles. Acrylic PSAs have been used for many years in medical and surgical applications. An outstanding acrylic copolymer, of the type described in U.S. Pat. No. 2,884,126/RE 24,906 (Ulrich) has been employed in a porous, surgical adhesive tape, U.S. Pat. No. 3,121,021 (Copeland) with very acceptable skin adhesion performance. The advantages of an acrylic PSA in medical applications, e.g., less irritation to the skin, as well as the disadvantages which result from adhesion buildup (compliance failure) when the acrylic PSA is in contact with the skin for long periods of time were recognised in U.S. Pat. No. 3,321,451 (Gander). According to the aforementioned Gander patent, the irritation caused by removal of the tape was overcome by including in the acrylate adhesive polymer certain amine salts which made it possible to remove the tape by washing with water, a procedure which is not always feasible where high standards of sterility must be maintained.

In U.S. Pat. No. 3,475,363 (Gander), the inventor has attempted to overcome the objectionable compliance failure in acrylate PSAs by employing as a crosslinking agent dimethylaminoethyl methacrylate to ensure adhesion to the skin without deleterious effects. U.S. Pat. No. 3,532,652 (Zang), recognize that acrylate PSAs are affected when used on surfaces which promote migration of oils and the like to the adhesive, thereby weakening their cohesive strength. Zang overcomes this problem by partially crosslinking his acrylate interpolymer with polyisocyanate. In U.S. Pat. No. 4,140,115 (Schonfeld), the inventor reduces the stripping of tissue cells when his acrylate PSA is removed from the skin by blending the PSA with an unreacted polyol having a fatty acid ester pendant moiety. This adhesive has a tendency to leave objectionable residue.

Another approach to modifying PSA tape for the purpose of controlling the degree of elastic compliance and viscous flow can be found in U.S. Pat. No. 4,260,659 (Gobran), which teaches how a plurality of superimposed adhesive layers having different gradients of shear creep compliance can meet the requirement of releasable adhesion to a plastic surface such as polyethylene. In U.S. Pat. No. 4,374,883 (Winslow), the shear creep compliance is achieved and the cohesive strength maintained by combining two layers of adhesive which reinforce each other. While both of these address the problem of modifying a PSA to improve compliance, neither deals with the kind of precision and control required in medical products which are adhered to the skin.

SUMMARY OF THE INVENTION

This invention provides a highly efficient method of crosslinking an acrylate PSA as compared with comparable conventional methods of crosslinking an acrylate PSA to obtain a pressure-sensitive adhesive having a degree of compliance sufficient to yield high adhesion to skin without objectionable adhesion build over time on the skin.

One aspect of this invention is a crosslinked pressure-sensitive adhesive comprising a crosslinked copolymer comprised of A monomers and PX monomers wherein:

A is a monomer acrylate or methacrylate ester of a non-tertiary alcohol or a mixture of non-tertiary alcohols, said alcohols having from 1 to 14 carbon atoms with the average number of carbon atoms being about 4–12; and PX is a copolymerizable mono-ethylenically unsaturated aromatic ketone monomer free of ortho-aromatic hydroxyl groups; the copolymer being crosslinked by means of said PX monomer and the degree of crosslinking and the degree of polymerization of the copolymer being such that the crosslinked pressure-sensitive adhesive composition has a creep compliance value (hereinafter J-value) of at least about $1.2 \times 10^{-5}$ cm$^2$/dyne.

Use of the PX monomer to crosslink the copolymer allows for control of the creep compliance of the adhesive. The PSA can be chemically tailored to produce within physically defined parameters a skin adhesive for a tape which is a significant advance over the prior art in its ability to conform to the human skin surface and be removed after a reasonable period of time without under irritation to the skin and without leaving objectionable residue. The optimization of these two properties without upsetting the delicate four-fold balance of adhesion, cohesion, stretchiness and elasticity has required a unique combination of polymerization techniques which control the rheological properties contributing to the bond-making (compliance) and the bond-breaking (release) properties of a PSA coated material which has been in moderately long contact with the human skin.

Another aspect of this invention is a pressure-sensitive adhesive precursor comprised of an uncrosslinked copolymer comprised of A monomers and PX monomers wherein the degree of polymerization of the copolymer and the degree of crosslinkability due the presence of the PX monomers is such that the pressure-sensitive adhesive precursor, when crosslinked by means of said PX monomer, will exhibit a creep compliance value of at least about $1.2 \times 10^{-5}$ cm$^3$/dyne.

Copolymerizing the PX monomer into the backbone of the pressure-sensitive adhesive copolymer allows for crosslinking of the copolymer with ultra-violet radiation after formation of the copolymer. Further, copolymerizing the PX monomer into the polymer backbone before the crosslinking thereof greatly increases the efficiency of the crosslinking obtainable by inclusion of the PX monomer in the adhesive as compared with addition of an aromatic ketone compound which is not initially copolymerized into the copolymer. Because of the increased efficiency, only small amounts of PX monomer are needed to achieve useful degrees of crosslinking.

The adhesive is preferably used as the adhesive layer of a tape. When the creep compliance of the pressure-sensitive adhesive of this invention is at least about $1.2 \times 10^{-5}$ cm$^2$/dyne, the tape, or a dressing bearing the adhesive, can be applied to skin such that the adhesive will exhibit an enhanced level of initial adhesion to the skin without objectionable adhesion build over time. Accordingly, an aspect of this invention is an article comprised of a support member having a surface, at least a portion of said surface coated with a pressure-sensitive adhesive as described above.

Another aspect of this invention is a method of preparing a pressure-sensitive adhesive coated article comprising:

(a) copolymerizing a mixture of A monomers and PX monomers wherein:

A is a monomeric acrylate or methacrylate ester of a non-tertiary alcohol or a mixture of non-tertiary alcohols, said alcohols having from 1 to 14 carbon atoms with the average number of carbon atoms being about 4–12; and PX is a copolymerizable mono-ethylenically unsaturated aromatic-ketone monomer free of ortho-aromatic hydroxyl groups, under conditions which will not cause the aromatic-ketone group to crosslink the copolymer;

(b) coating at least a portion of a surface of a support member with the uncrosslinked copolymer, and (c) exposing the coated uncrosslinked copolymer to ultraviolet radiation which will crosslink the copolymer by means of the aromatic ketone groups; wherein the degree of crosslinking and the degree of polymerization of the copolymer are such that the crosslinked copolymer has a creep compliance value of at least about $1.2 \times 10.5$ cm$^2$/dyne.

The method of this invention allows for the use of solventless coating techniques because the copolymer is not crosslinked until after it is coated upon a support member.

DETAILED DESCRIPTION OF THE INVENTION

Figure 1:
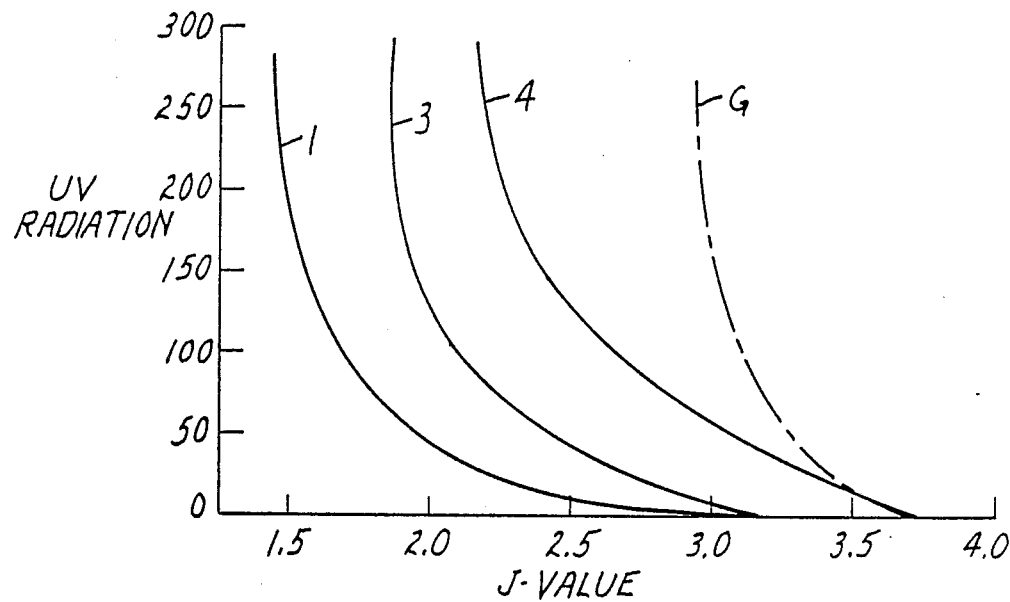
FIGS. 1–6 are plots of compliance of a pressure-sensitive adhesive as measured by its J-value in cm$^2$/dyne versus ultraviolet radiation intensity for crosslinked and uncrosslinked adhesives.

The pressure-sensitive adhesive composition is prepared from an uncrosslinked, but crosslinkable, copolymer precursor which consists essentially of copolymerized A and PX monomers and optional B monomers.

The number and composition of A, PX and B monomers and the degree of polymerization of the copolymer are preferably adjusted to obtain the desired degree of creep compliance. For a polymer having a given A and B composition, an increase in the amount of PX monomer will result in an increase in the degree of photocrosslinking and decrease the level of creep compliance of the copolymer. Likewise, an increase in the degree of polymerization of the copolymer will decrease the level of creep compliance of the adhesive. Accordingly, as the amount of PX monomer is increased and, as a result, the degree of photocrosslinking is increased, the degree of polymerization of the copolymer adhesive should be decreased to obtain a comparable level of creep compliance. Conversely, if the amount of PX monomer is decreased, and, as a result, the degree of photocrosslinking is decreased, the degree of polymerization of the uncrosslinked copolymer adhesive should be increased to obtain a comparable level of creep compliance when crosslinked. For example, a preferred composition of the copolymer adhesive is 98 parts isooctyl acrylate, 0.05 part para-acryloxy benzophenone and 2 parts acrylic acid. For this particular composition, the inherent viscosity, which is a measure of the degree of polymerization of the resulting copolymer before crosslinking, should be from about 0.85 to about 0.95 dl/g.

To obtain the desired degree of compliance, the weight of PX monomer is generally within the range of about 0.01% to about 2%, preferably about 0.025% to about 0.5% of the total weight of all monomers in the copolymer. Levels of PX monomer of 2% or greater are preferably avoided in adhesives for medical use due to an objectionable decrease in the compliance of the resulting adhesive.

In general, the inherent viscosity of the uncrosslinked copolymer should range from about 0.5 to about 1.4 dl/g, more preferably 0.55 to 1.1, to obtain the desired degree of polymerization of the copolymer. The test procedure followed and the apparatus that can be used to measure inherent viscosity are described in detail in "Textbook of Polymer Science", F. W. Billmeyer, Wiley-Interscience, Second Edition, 1971, Pages 84 and 85.

Monomer A is a monomer which contributes to the visco-elastic properties of the copolymer, i.e., monomer A is a monomeric acrylic or methacrylic acid ester of a non-tertiary alcohol or a mixture of non-tertiary alcohols, said alcohols having from 1 to 14 carbon atoms with the average number of carbon atoms being about 4–12. Examples of such monomers include the esters of acrylic acid or methacrylic acid with non-tertiary alkyl alcohols such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art and many are commercially available.

The PX monomer is a copolymerizable monoethylenically unsaturated aromatic ketone compound free of ortho-aromatic hydroxyl groups, wherein only the ethylenically unsaturated group is copolymerizable with the A monomers and optional B monomers under the polymerization conditions selected to form the copolymer.

Aromatic ketones free of ortho-aromatic hydroxyl groups absorb ultraviolet radiation to form a triplet excited state through intersystem crossing. These excited state molecules can abstract hydrogen radicals from the polymer. The free radical sites thus generated on the polymer can combine to form crosslinks. The semi-pinacol radical which results from the combination of the photocrosslinker (PX) and the hydrogen radical can also lead to crosslinking since the photocrosslinker is copolymerized. The presence of a hydroxyl group as ring substituent in a position ortho to the carbonyl on the aromatic ring will inhibit the crosslinking ability of the aromatic ketone monomer. Accordingly, the aromatic-ketone monomer is free of ortho-aromatic hydroxyl groups.

Preferred PX monomers are represented by the general formula

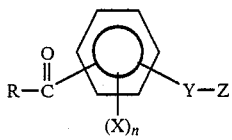

wherein
R is lower alkyl or phenyl, provided that R may be substituted with one or more halogen atoms, alkoxy groups, or hydroxyl groups, and further provided that when R is phenyl substituted with one or more hydroxyl groups, any such hydroxyl groups must be meta or para to the aromatic carbonyl, X is halogen, alkoxy, or hydroxyl, provided that when an X is a hydroxyl group, X must be meta or para to the aromatic carbonyl, n is an integer from 0 to 4.

Y is a divalent linking group, preferably selected from the group consisting of a covalent bond, an oxygen atom (—O—), an amino group (—NR'— wherein R is hydrogen or lower alkyl), an oxyalkyleneoxy group (—O—R"—O— wherein R" is an alkylene group), a carbamoylalkyleneoxy group (—O—R"—O—C(O)—N—(R')—R'"— wherein R'" is a covalent bond or an alkyleneoxy group such as —R"—O— wherein R" is an alkylene group), and Z is alkenyl or ethylenically unsaturated acyl.

Particularly preferred PX monomers are the acryloxybenzophenones, e.g. para-acryloxybenzophenone.

The optional B monomer is an ethylenically unsaturated compound copolymerizable with the monomeric acrylic acid ester and is employed to modify the physical properties of the copolymer. In general, the addition of the B monomer will reduce the flexibility of the copolymer. Preferred B monomers are acrylic acid, methacrylic acid, itaconic acid, acrylamide, methacrylamide, acrylonitrile, methacrylonitrile, vinyl acetate, and N-vinylpyrrolidone. The B monomer may be included at levels up to 25% of the total weight of all monomers. The preferred adhesive according to the present invention will contain from about 1% to about 15% by weight of B monomer of the total weight of all monomers. In the preferred skin adhesive, the amount of acrylic acid or acrylamide will range from about 1% to about 4% by weight of total monomer. In adhesives containing N-vinylpyrrolidone as the B monomer, the preferred copolymer will contain from about 5% to about 15% of N-vinylpyrrolidone by weight.

The A monomer, PX monomer, and optional B monomer may be dissolved in a suitable inert organic solvent and polymerized by standard free radical polymerization utilizing a suitable free radical initiator such as those described in U.S. Pat. No. Re 24906 (Ulrich). Suitable initiators which may be utilized include azo compounds such as 2,2'-azo-bis(isobutyronitrile), hydroperoxides such as tert-butyl hydroperoxide, peroxides such as benzoyl peroxide or cyclohexanone peroxide. Generally, from about 0.01% to about 1% by weight of thermally activatable initiator based upon the total polymerizable composition is used, preferably 0.01% to 0.5%.

The organic solvent utilized in the free radical polymerization may be any organic liquid which is a solvent for the reactants and product, that is inert to the reactants and product, and will not otherwise adversely affect the reaction. Suitable solvents include ethyl acetate and mixtures such as ethyl acetate with toluene, heptane and toluene and isopropyl alcohol and heptane with toluene and methyl alcohol. Other solvent systems are useful. The amount of solvent is generally about 30–80% by weight based on the total weight of the reactants and solvent. Copolymerization may be carried out by other well known techniques such as suspensions, emulsion or bulk polymerization.

The uncrosslinked copolymer is easily coated upon suitable backings which may include woven, nonwoven or knit fabric, or medium to low tensile modulus films such as polypropylene, polyethylene, polyvinyl chloride, polyurethane, polyester, and ethyl cellulose. Conformable synthetic film backings for medical applications will have a tensile modulus of less than about 400,000 psi as measured in accordance with ASTM D-630, preferably less than about 300,000 psi.

Woven and nonwoven fabric backings can be formed of threads of synthetic or natural materials such as cotton, nylon, rayon, polyester, and the like.

Preferred backings for medical applications are those which permit transpiration of perspiration and/or tissue or wound exudate therethrough, e.g., nonwoven fabrics, woven fabrics, knits and the like. Accordingly, preferred backings for medical applications have a high rate of moisture vapor transmission therethrough, i.e., of at least about 500 g/m$^2$, over 24 hours at 100° F. (38° C.) with a humidity differential of 80%, more preferably at least about 1000 g/m$^2$ when tested in accordance with ASTM E 96-80. For example, a continuous film backing prepared from a polyurethane sold under the tradename "Estane", available from B. F. Goodrich, and a continuous film backing prepared from a polyester sold under the tradename "Hytrel", available from DuPont, each have values of about 1000 to about 1500 g/m$^2$. Woven backings such that those used for Durapore TM brand surgical tape, available from 3M, Co. have even higher values. In contrast, conventional polyethylene terephthalate films have approximate values of about 50 g/m$^2$.

The coated sheet materials may take the form of any article conventionally used with skin adhesives such as tapes, patches, strips, wound dressings, monitoring or neuro-stimulating electrodes, drapes or the like. These articles may be dispensed from any convenient dispensing form, e.g., multi-layered pads, etc.

The uncrosslinked copolymer precursor can be applied by any of a variety of conventional techniques such as roll coating, spray coating, curtain coating, and the like, the particular method selected depending upon the nature of the backing being employed. For example, where the backing is a nonwoven fabric, a suitable method for applying the uncrosslinked copolymer precursor thereto involves coating a solution of the adhesive copolymer in an organic solvent onto a release liner, followed by lamination of the nonwoven fabric backing to the (semi-dry) adhesive coating. The precursor can be coated without modification by extrusion coating, coextrusion, hot-melt coating and the like by employing suitable conventional coating devices for this purpose. Primers can be used but they are not always necessary depending on the nature of the backing.

After the adhesive has been coated, it is subjected to ultraviolet radiation of sufficient intensity for a time sufficient to crosslink the copolymer to the desired degree by means of the aromatic ketone groups of the PX monomer. The degree of crosslinking by means of the PX monomer is controlled by the amount of PX monomer in the copolymer and the intensity of the crosslinking radiation to which the uncrosslinked copolymer is exposed during the method of preparing an adhesive of this invention.

While it is possible to use a comparative excess of PX monomer and adjust the degree of crosslinking by controlling the intensity of the radiation to which the uncrosslinked copolymer is exposed, the degree of crosslinking is preferably controlled by using a comparative excess of radiation and by adjusting the amount of PX monomer in the uncrosslinked copolymer. In this preferred method of preparing the adhesives of this invention, the use of commercially-available medium pressure mercury lamps having an output of about 80 watts per cm (200 watts per inch) and having a spectral output over a range of 180 to 430 nanometers is preferred. The exposure is determined by the speed at which the adhesive-coated sheet moves beneath the lamps and the distance between the lamps and the exposed surface. The exposure can be measured using an integrating radiometer (Dynachem TM Model 500) available from Dynachem Corporation, 2631 Michelle Drive, Tustin, CA 92680. The amount of radiant energy is measured in millijoules per square centimeter. For the examples set forth below, the dose ranged from 10 to 3000 millijoules and was not limiting because the adhesives were relatively transparent and were coated at thicknesses ranging from 12 micrometers to 50 micrometers (from 0.5 to 2.0 mils).

The adhesives of this invention may also be used in a method of adhering an adherend to a substrate. In this method, an effective amount of an adhesive of this invention is interposed between the adherend and a substrate and pressure is applied to activate the adhesive. The adherend is preferably a sheet material as described above which is applied to the skin as a cover, patch or tape for the conventional purposes thereof and, for medical applications, the substrate is generally skin.

In one embodiment, the adhesive of this invention can be coated between two release liners and then crosslinked. To use this embodiment, a release liner is removed and the exposed adhesive is pressed against a substrate. The other release liner is then removed and the adherend is pressed onto the exposed adhesive.

In order to understand the advantages of this invention, it is necessary to understand how a fundamental rheological property of the pressure sensitive adhesives being used enables one to ascertain when and how the advantages of the invention are being obtained. The measurement of this property, which is the creep compliance of the PSA used to coat the tape backing, will be covered in detail later. The fundamentals of creep compliance as they relate to polymeric materials and, in particular, to viscoelastic polymers is covered in "Viscoelastic Properties of Polymers", John D. Ferry, 3rd Edition, John Wiley and Sons, 1980, Chapter 1. Also in "Treatise on Adhesion and Adhesives", Volume 2, "Materials", "Pressure Sensitive Adhesives", R. L. Patrick, Editor, Marcel Dekker, Inc., 1969. In "Properties and Structure of Polymers", Tobolsky, John Wiley and Sons, 1960, Chapter II, Section 6, the five regions of viscoelastic behavior are discussed. C. A. Dahlquist in "Handbook of Pressure Sensitive Adhesive Technology", edited by Donatas Satas, Van Nostrand Reinhold Company, 1982, Chapter 5 discusses how the stress-strain behavior of pressure-sensitive adhesives can be treated as a creep compliance phenomenon.

CREEP COMPLIANCE PROCEDURE

To measure the creep compliance of the skin adhesive of this invention, a 150-micrometer thickness of the adhesive is knife-coated onto a smooth film of polytetrafluoroethylene. The coated film is then dried to constant weight by placing it in an air-circulating oven generally for at least five minutes at 110° C. The skin adhesive, thus dried, is stripped from the polytetrafluoroethylene and two test pieces of equal area are die-cut and placed in the parallel plate creep compliance rheometer, one piece being on each side of the center plate, with an outer plate contacting the exposed surface of each. Screws which connect the two outer plates are then tightened so as to compress the interposed layers of skin adhesive approximately 10%. The parallel plates are placed in horizontal arrangement and one end of the center plate is connected to a chart recorder. A hook is attached to the opposite end of the center plate with a flexible wire extending horizontally from the hook and then downward over a pulley, the outer plates being held in a fixed position. A suitable weight (one sufficient to measurably deform the sample a distance no greater than its thickness) is attached to the free end of the wire, then the strip chart recorder is started. The weight typically used to exert the stress on the skin adhesive films is 500 grams. From the strip chart recorder, the time and the displacement (strain) are read and the applied force (stress) is recorded. The creep compliance at a given temperature is then calculated using the equation:

$$J_{(t)} = \frac{2A X}{hf},$$

where t is the time at which the measurement is taken, A is the area of one face of the adhesive samples, h is the thickness of the adhesive mass, X is the displacement at time t (where X is less than h) and f is the force due to the mass attached to the wire connected to the middle plate. Where A is expressed in $cm^2$, h in cm, X in cm, and f in dynes, the compliance value $J_{(t)}$ is given in $cm^2$/dyne.

It has been found that the skin adhesive films of this invention have the required degree of compliance and the short term creep to function as an exceptionally fine pressure sensitive skin adhesive for medical and surgical applications, when the J value measured at ambient conditions at the end of a 3 minute period of subjection to stress is at least about $1.2 \times 10^{-5}$ $cm^2$/dyne to about $2.3 \times 10^{-5}$ $cm^2$/dyne, preferably about $1.3 \times 10^{-5}$ $cm^2$/dyne to about $2.0 \times 10^{-5}$ $cm^2$/dyne. It has been found that the higher the creep compliance, the greater the adhesive residue left on the skin after removal of the skin adhesive coated sheet material. Accordingly, creep compliance values greater than $2.3 \times 10^{-5}$ $cm^2$/dyne are not preferred.

SKIN ADHESION PROCEDURE

The evaluation of the skin adhesives of this invention is highly subjective when the performance in contact with and upon removal from the human skin surface becomes part of the evaluation. For this reason a protocol was developed using a prescribed test panel of individuals who were selected to embrace the normal variations in skin surface that are encountered in medical practice. The result of this designed study enables one to get values which can be considered controlled and comparative. While these values are observational in respect to adhesive residue, sample lift and adhesion build-up, the procedures followed are in accord with carefully developed assessments of similar properties as is known in the art.

The initial skin adhesion value ($T_o$) and the skin adhesion value after 24 or 48 hours in contact with the skin ($T_{24}$ or $T_{48}$) are essentially the widely accepted PSTC-1, peel adhesion test for single coated skin adhesive tapes measured at 180° angle. PSTC-1 is test method No. 1 of the Pressure Sensitive Tape Council, Glenview, Ill., Seventh Edition (1976); developed by the Specifications and Technical Committee of the Council. The test has been modified only to the extent that the tape is applied to the human skin surface on a selected area on the individual's back. Otherwise the steps in the procedure are as follows:

1. Tape samples 2.54 cm wide by 5.08 cm long are placed on the back of a human subject.
2. Each tape is rolled down with one forward and one reverse pass, using a 1-kilogram tape roller (described in Appendix B, Sections 2.7.1, 2.8.1 and 2.8.2 of Pressure Sensitive Tape Council) moved at the rate of about 30 cm per minute.
3. Adhesion to the skin is measured as the peel force required to remove the tape at 180° angle (PSTC-1). The peel force values are measured through the use of a strain-gauge mounted on a motor-driven carriage. The force of removal is reported in grams of adhesion per 2.54 cm of width of sample. The rate of removal is 15 cm per minute.
4. The adhesion to skin is measured immediately after initial application ($T_o$) and after 24 or 48 hours of continuous contact with the skin ($T_{24}$ or $T_{48}$).

Preferred skin adhesive will generally exhibit a $T_o$ of between 50 grams to about 100 grams and a $T_{48}$ of between about 150 grams to about 300 grams.

Adhesive Residue Test

When the skin adhesion test described above is performed, the skin underlying the tape sample is visually inspected to determine the amount of adhesive residue left on the surface of the skin. Each sample is assigned a numerical rating from 0 to 5 based on the following scale.

| Rating | Definition |
| --- | --- |
| 0 | No visible residue; |
| 1 | Only residue at edges of tape; |
| 2 | Residue covering 1% to 25% of tested area; |
| 3 | Residue covering 25% to 50% of tested area; |
| 4 | Residue covering 50% to 75% of tested area; |
| 5 | Residue covering 75% to 100% of tested area. |

The results of all tape samples of a given panel were averaged and are reported below. Due to the subjectivity of the visual inspection for residue, no degree of precision should be inferred from the numbers to the right of the decimal point and those numbers should be treated as only rough approximations.

Preferred skin adhesives will generally exhibit an average residue rating below about 2.5.

EXAMPLES A-F

Preparation of Crosslinkers

EXAMPLE A

Preparation of para-acryloxybenzophenone (ABP)

A three-neck round-bottom flask fitted with an addition funnel, thermometer and a mechanical stirrer was charged with 100 ml of water, 40 g (0.20M) of p-hydroxybenzophenone and 8.8 g of sodium hydroxide. The flask was cooled in an ice bath to 8°-10° C., then 20 g (0.22) of acryloyl chloride were added dropwise while holding the temperature at 8°-10° C. When the addition was complete, the reaction mixture was stirred for an additional half hour. Then 150 ml of diethyl ether was added to dissolve the product of the reaction. The ether layer was separated from the water layer and washed twice with 3% sodium hydroxide and twice with water. The solution was dried over magnesium sulfate, filtered and stripped. An amount of 43.0 g of an oily product was obtained and purified by recrystallization from absolute ethanol, from which an amount of about 34.7 g of white crystalline product was isolated.

EXAMPLE B

Preparation of para-acryloxyethoxybenzophenone (EABP)

Step 1 A three-neck round-bottom 1000-ml reaction flask fitted with a magnetic stirrer, heating mantle and condenser, thermometer and dropping funnel was charged with 250 ml of water, 23.0 g (0.58M) of sodium hydroxide and 99.0 g (0.50M) of 4-hydroxybenzophenone. The reaction mixture was stirred until a red-brown solution was obtained. Then, 44.0 g (0.55M) of 2-chloroethanol was added and the mixture was heated at reflux temperature for 16 hours. After cooling to room temperature, the reaction separated into two layers. The bottom layer was dissolved in an equal amount of dichloromethane, washed twice with 10% sodium hydroxide and twice with 2% sodium chloride, and then dried over magnesium sulfate. The solution was filtered and stripped to give 67.0 g of crude product. This crude product was recrystallized from ethyl acetate to yield 37.4 g of pure product.

Step 2 For this next step in the preparation of (EABP), 20.0 g (0.08M) of the recrystallized product from Step A of this procedure plus 20.0 g (0.28M) of acrylic acid, 300 g of toluene, 0.1 g of phenothiazine and 6.0 g of p-toluenesulfonic acid were added to a 1000-ml two-neck round-bottom reaction flask fitted with Dean-Stark trap, a condenser and a magnetic stirrer. The reaction was heated at reflux temperature for 18 hours. After cooling to room temperature, 10 g of calcium hydroxide were added followed by two hours of stirring. The solution was filtered, then stripped to give 20.6 g of a viscous oil. A white solid product was finally obtained by recrystallizing the oil from absolute ethanol.

EXAMPLE C

Preparation of para-N-(methacryloxyethyl)carbamoylethoxybenzophenone (IEMBP)

The recrystallized product from Step 1 in the preparation of (EABP) was used for the preparation of (IEMBP).

An amount of 5.2 g (0.02M) of the recrystallized product from Step 1 of Example B, 3.3 g (0.02M) of 2-isocyanatoethyl methacrylate and 0.35 g of phenothiazene was dissolved in 100 g of toluene in a 250-ml three-neck round-bottom reaction flask fitted with a condenser, heating mantle, magnetic stirrer and a nitrogen inlet. The reaction mixture was heated for one hour at 50° C. A drop of tin octoate catalyst was added and heating at 50° C. continued for two more hours. After cooling to room temperature the solvent was stripped off yielding a viscous oil. The oil solidified upon standing for several hours at room temperature. White crystals were obtained by recrystallization from toluene.

EXAMPLE D

Preparation of para-acryloxyacetophenone (p-AAP)

To prepare para-acryloxy acetophenone, 100 ml water, 13.0 g sodium hydroxide and 40.0 g p-hydroxyacetophenone were added to a three-neck round-bottom flask fitted with a mechanical stirrer, thermometer and an ice bath. The reaction was cooled to 10°-15° C. and 29.0 g of acryloyl chloride was added dropwise over 30 minutes. The mixture was stirred for two hours with warming to room temperature. 150 ml of diethyl ether was added and the ether solution was separated from the water in a separatory funnel. The ether layer was washed with 3% sodium hydroxide solution three times and with water two times. The solution was dried over magnesium sulfate, filtered and stripped to isolate a solid residue. The residue was recrystallized five times from ethanol to yield 7 g pure white crystals.

EXAMPLE E

Preparation of ortho-acryloxyacetophenone (o-AAP)

To prepare o-acryloxyacetophenone, 200 ml water, 13.0 g sodium hydroxide and 40.0 g o-hydroxy acetophenone were added to a three-neck round-bottom flask fitted with a mechanical stirrer, thermometer and an ice bath. The reaction was cooled to 10°-15° C. and 29.0 g of acryloyl chloride were added dropwise over 30 minutes. The reaction mixture was stirred for two hours while warming to room temperature. 150 ml of diethyl ether was added and the ether solution was separated form the water in a separatory funnel. The water layer was extracted with an additional 150 ml of ether. The ether extracts were combined and washed three times with 3% sodium hydroxide solution, and two times with water. The ether solution was separated and then dried over magnesium sulfate. The magnesium sulfate was filtered off and the ether was stripped off on a rotary evaporator. The liquid residue was distilled at 104° C. and 0.8 m mercury to isolate 23.1 g of clear water-white liquid.

EXAMPLE F

Preparation of ortho-acrylamidoacetophenone (o-ACMAP)

To prepare ortho-acrylamidoacetophenone, 200 ml water and 20 g sodium hydroxide were added to a 500-ml three-neck round-bottom flask fitted with a mechanical stirrer, thermometer, addition funnel, and an ice bath. 40 g o-aminoacetophenone were added and the mixture was cooled to 10°-15° C. 29 g acryloyl chloride were added dropwise with stirring. Stirring was continued with cooling for an additional two hours. Next 200 ml of diethyl ether was added and the ether solution was separated form the water layer in a separatory funnel. The ether solution was washed two times with 200 ml of 5% HCl and two times with 200 ml of water. The ether solution was dried over magnesium sulfate, filtered and the ether was stripped on the rotary evaporator. The residue was recrystallized from 95% ethanol to isolate 19 g of yellow crystals.

EXAMPLES G-I and 1-20

Uncrosslinked Adhesive Precursors

The adhesive formulations wwere prepared with different amounts of several photocrosslinkers. These formulations were isooctyl acrylate/acrylic acid (IOA/AA) at an approximate ratio of 98/2, isooctyl acrylate/acrylamide (IOA/ACM) at an approximate ratio at 98/2, and isooctyl acrylate/N-vinyl pyrrolidone (IOA/NVP) at an approximate ratio of 90/10. The exact charges for each adhesive are given in Tables I, II and III. The precursors were prepared by charging the monomers, solvent, initiator (2,2'-azobisisobutryonitrile available from duPont as VAZO ™ 64) and chain transfer agent ($CBr_4$) to 1-liter amber bottles, purging with nitrogen at 1 liter/min for 2 minutes, sealing the bottles and heating at 55° C. for 24 hours while tumbling in a water bath.

TABLE I

| | Acrylic Acid Copolymers | | | | |
|---|---|---|---|---|---|
| Example: | G | 1 | 2 | 3 | 4 |
| IOA (g) | 154.0 | 153.9 | 154.5 | 153.94 | 153.94 |
| AA (g) | 3.2 | 3.2 | 3.2 | 3.2 | 3.2 |
| 1% CBr$_4$ in IOA (g) | 2.8 | 2.8 | 2.2 | 2.8 | 2.8 |
| VAZO (g) | 0.48 | 0.48 | 0.48 | 0.48 | 0.48 |
| EtOAc (g) | 240.0 | 240.0 | 240.0 | 240.0 | 240.0 |
| PX/amount (g) | none | A/0.08 | A/0.16 | D/0.06 | E/0.06 |
| wt % PX | none | 0.05 | 0.10 | 0.038 | 0.038 |

TABLE II

| | Acrylamide Copolymers | | | | | | | | |
|---|---|---|---|---|---|---|---|---|---|
| Example: | H | 5 | 6 | 7 | 8 | 9 | 10 | 11 | 12 |
| IOA (g) | 151.6 | 151.52 | 152.48 | 152.64 | 151.54 | 151.54 | 151.51 | 151.51 | 151.51 |
| ACM (g) | 3.2 | 3.2 | 3.2 | 3.2 | 3.2 | 3.2 | 3.2 | 3.2 | 3.2 |
| 1% CBr$_4$ in IOA (g) | 5.2 | 5.2 | 5.2 | 4.0 | 5.2 | 5.2 | 5.2 | 5.2 | 5.2 |
| VAZO (g) | 0.48 | 0.48 | 0.48 | 0.48 | 0.48 | 0.48 | 0.48 | 0.48 | 0.48 |
| EtOAc (g) | 240.0 | 240.0 | 240.0 | 240.0 | 240.0 | 240.0 | 240.0 | 240.0 | 240.0 |
| PX/amount (g) | none | A/0.08 | A/0.12 | A/0.16 | D/0.06 | E/0.06 | D/0.09 | E/0.09 | F/0.09 |
| wt. % PX | none | 0.05 | 0.075 | 0.10 | 0.038 | 0.038 | 0.056 | 0.056 | 0.056 |

TABLE III

| | N—vinylpyrrolidone copolymers | | | | | |
|---|---|---|---|---|---|---|
| Example: | I | 13 | 14 | 15 | 16 | 17 |
| IOA (g) | 146.46 | 146.25 | 146.25 | 146.25 | 146.30 | 146.30 |
| NVP (g) | 16.25 | 16.25 | 16.29 | 16.29 | 16.25 | 16.25 |
| VAZO (g) | 0.49 | 0.49 | 0.49 | 0.49 | 0.49 | 0.49 |
| Heptane (g) | 91.0 | 91.0 | 91.0 | 91.0 | 91.0 | 91.0 |
| Toluene (g) | 39.0 | 39.0 | 39.0 | 39.0 | 39.0 | 39.0 |
| Methanol (g) | 32.5 | 32.5 | 32.5 | 32.5 | 32.5 | 32.5 |
| PX/amount (g) | none | A/0.21 | A/0.25 | A/0.29 | D/0.15 | E/0.15 |
| wt % PX | none | 0.129 | 0.154 | 0.178 | 0.092 | 0.092 |

Three representative formulations at three levels of photocrosslinker are given below in Table IV.

TABLE IV

| | Example: | | |
|---|---|---|---|
| | 18 IOA/NVP (90/10) | 19 IOA/AA (98/2) | 20 IOA/ACM (98/2) |
| IOA (g) | 146.25 | 153.90 | 152.64 |
| AA (g) | none | 3.20 | none |
| ACM (g) | none | none | 3.2 |
| NVP (g) | 16.29 | none | none |
| 1% CBr$_4$ in IOA (g) | none | 2.80 | 4.0 |
| VAZO (g) | 0.49 | 0.48 | 0.48 |
| Heptane (g) | 91.0 | none | none |
| Toluene (g) | 39.0 | none | none |
| Methanol (g) | 32.5 | none | none |
| EtOAc (g) | none | 240.0 | 240.0 |
| PX-A (g) | 0.25 | 0.08 | 0.16 |
| Wt % PX-A | 0.15 | 0.05 | 0.1 |

EXAMPLES OF CROSSLINKED ADHESIVES

Representative adhesive precursors of Examples G-I and 1-20 were coated at a thickness of 150 micrometers onto a smooth film of polytetrafluoroethylene and irradiated by use of a medium pressure mercury lamp available from Radiation Polymer Co., Plainfield, Ill. with an output of 200 watts per lineal inch. The rate of irradiation was adjusted to yield the exposure in millijoules per cm$^2$ shown in Tables V-X.

The resulting crosslinked adhesives exhibit the J values shown in Tables V through X.

TABLE V

| | Uncrosslinked Adhesive Precursor of Example: | | | |
|---|---|---|---|---|
| Intensity of Radiation (mj/cm$^2$) | G | 1 | 3 | 4 |
| | J values × 10$^{-5}$ (cm$^2$/dyne) | | | |
| 0 | 3.7 | 3.44 | 3.13 | 3.72 |
| 33 | 3.25 | 2.09 | 2.78 | 3.06 |
| 66 | 3.28 | 1.82 | 2.24 | 2.7 |
| 133 | 2.99 | 1.49 | 1.89 | 3.08 |
| 266 | 3.01 | 1.51 | 1.99 | 2.23 |

The data set forth above are graphically illustrated in FIG. 1.

TABLE VI

| | Uncrosslinked Adhesive Precursor of Example: | | | |
|---|---|---|---|---|
| Intensity of Radiation (mj/cm$^2$) | H | 5 | 8 | 9 |
| | J values × 10$^{-5}$ (cm$^2$/dyne) | | | |
| 0 | 3.09 | 3.43 | 2.9 | 2.8 |
| 33 | 3.12 | 2.2 | 2.63 | 3.06 |
| 66 | 2.86 | 1.8 | 2.16 | 2.44 |
| 133 | 2.44 | 1.53 | 1.69 | 2.28 |
| 266 | 2.37 | 1.51 | 1.39 | 1.95 |

Figure 2:
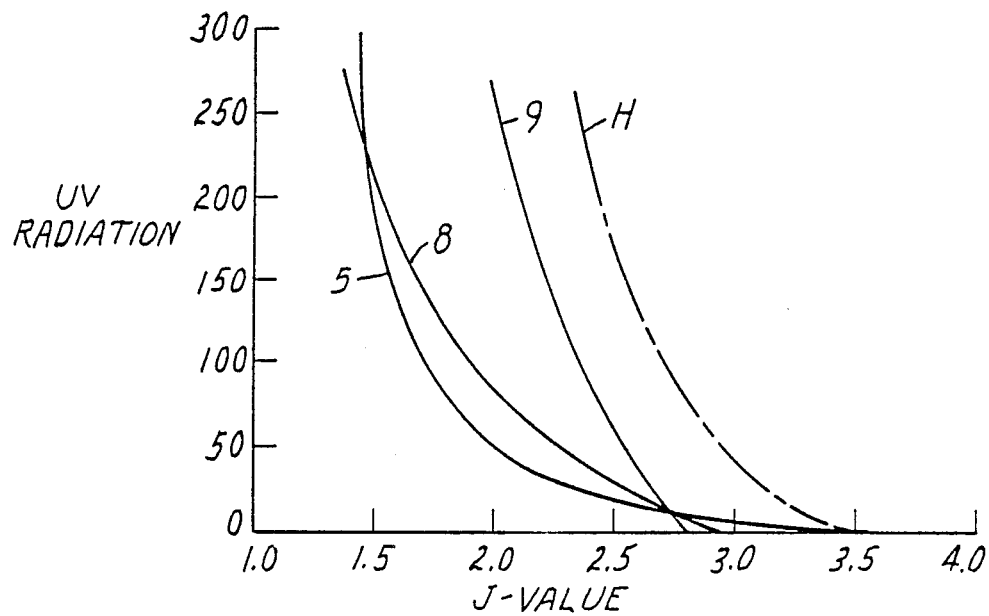

The data set forth in Table VI above are graphically illustrated in FIG. 2.

TABLE VII

| | Uncrosslinked Adhesive Precursor of Example: | | | |
|---|---|---|---|---|
| Intensity of Radiation (mj/cm$^2$) | 6 | 10 | 11 | 12 |
| | J values × 10$^{-5}$ (cm$^2$/dyne) | | | |
| 0 | 3.65 | 3.78 | 3.83 | 3.67 |
| 33 | 2.17 | 2.41 | 3.5 | 3.96 |
| 66 | 1.48 | 2.15 | 3.4 | 3.53 |
| 133 | 1.29 | 1.77 | 2.59 | 3.70 |
| 266 | 1.08 | 1.44 | 2.05 | 3.05 |

Figure 3:
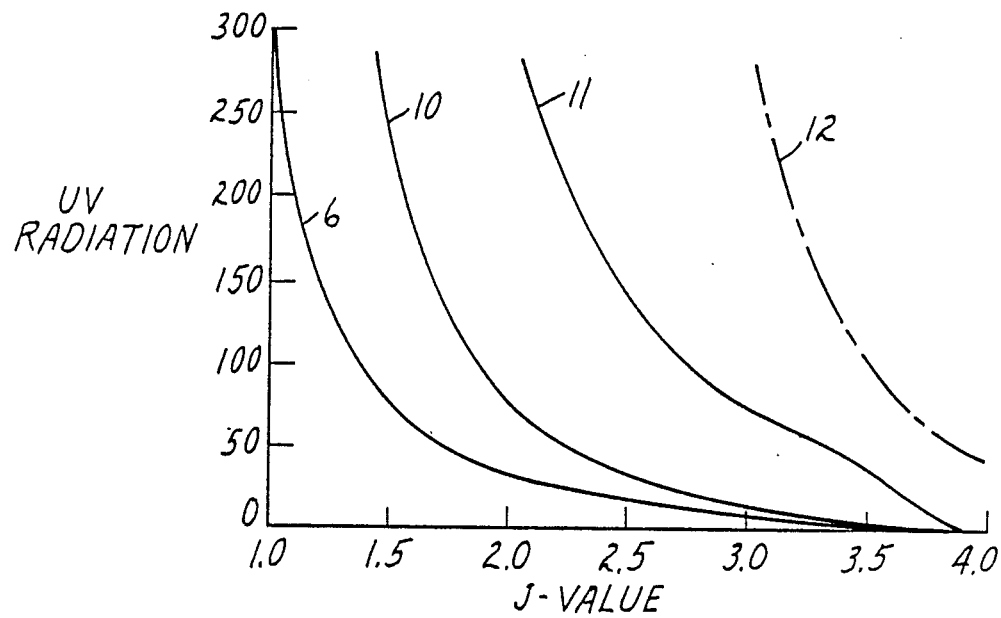

The data set forth in Table VII above are graphically illustrated in FIG. 3.

TABLE VIII

| | Uncrosslinked Adhesive Precursor of Example: | |
|---|---|---|
| Intensity of Radiation (mj/cm$^2$) | 2 | 7 |
| | J values × 10$^{-5}$ (cm$^2$/dyne) | |
| 50 | 1.32 | 1.4 |
| 100 | 1.24 | 1.36 |
| 200 | 1.01 | 1.24 |
| 300 | 1.01 | 1.12 |

Figure 4:
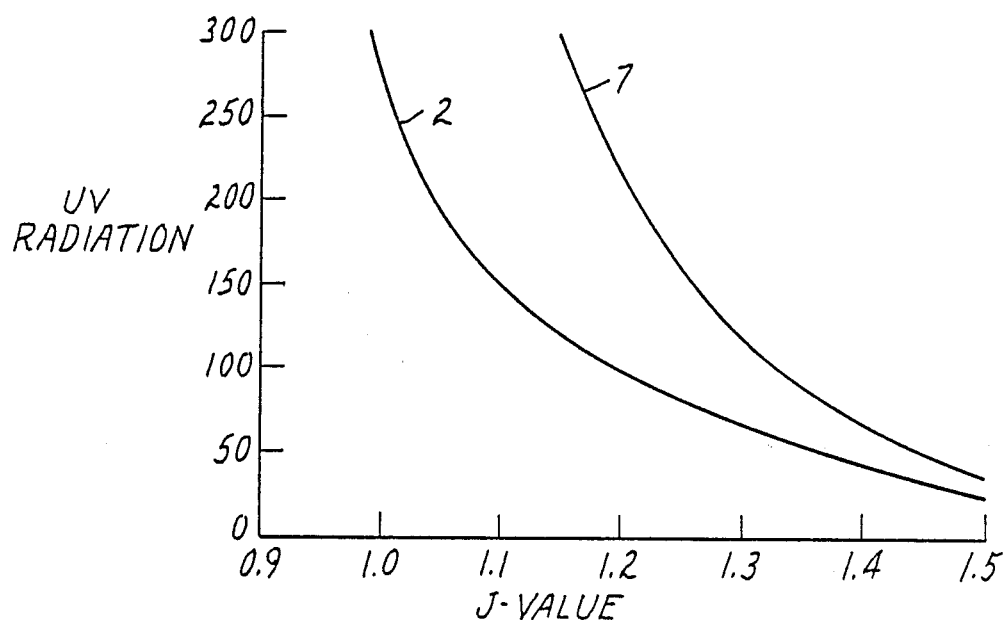

The data set forth in Table VIII are graphically illustrated in FIG. 4.

TABLE IX

| Intensity of Radiation (mj/cm$^2$) | Uncrosslinked Adhesive Precursor of Example: | | | |
|---|---|---|---|---|
| | 1 | 13 | 16 | 17 |
| | J values × 10$^{-5}$ (cm$^2$/dyne) | | | |
| 0 | 8.22 | 8.89 | 8.47 | 8.31 |
| 33 | 8.4 | 2.61 | 5.14 | 7.18 |
| 66 | 8.9 | 2.09 | 4.05 | 6.57 |
| 133 | 8.27 | 1.98 | 2.52 | 5.3 |
| 266 | 7.47 | 1.71 | 2.03 | 4.12 |

Figure 5:
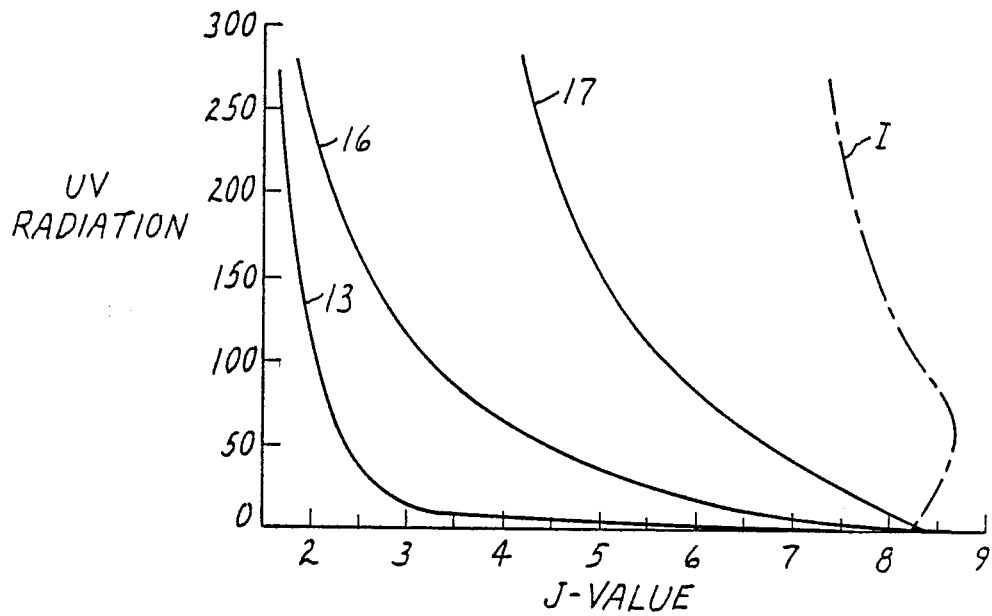

The data set forth in Table IX above are graphically illustrated in FIG. 5.

TABLE X

| Intensity of Radiation (mj/cm$^2$) | Uncrosslinked Adhesive Precursor of Example: | | |
|---|---|---|---|
| | 13 | 14 | 15 |
| | J values × 10$^{-5}$ (cm$^2$/dyne) | | |
| 50 | 2.48 | 2.48 | 1.9 |
| 100 | 2.41 | 2.28 | 1.82 |
| 200 | 2.13 | 1.86 | 1.48 |
| 300 | 1.98 | 1.74 | 1.29 |

Figure 6:
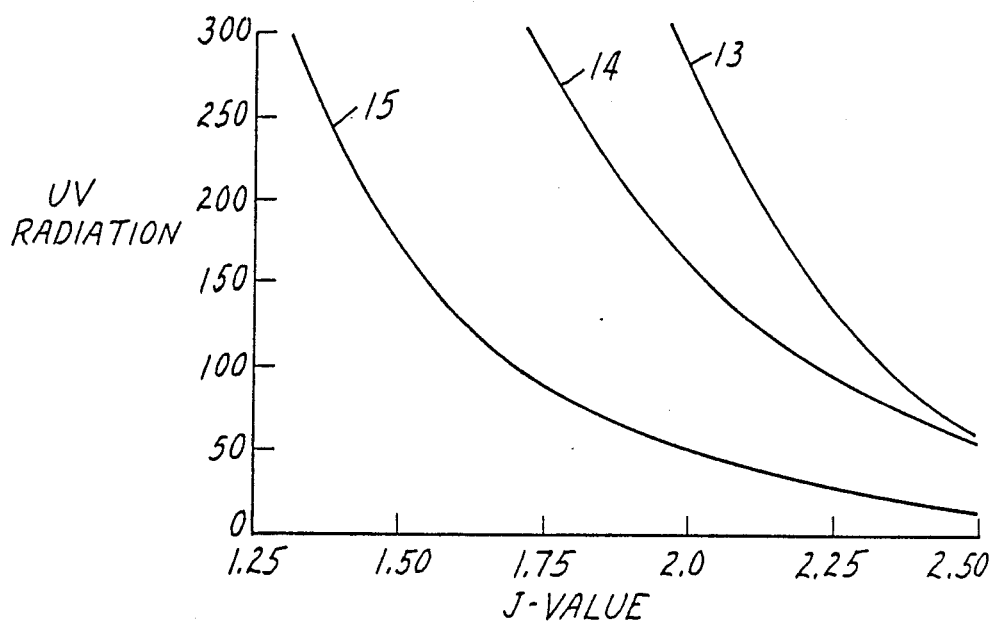

The data set forth in Table X above are graphically illustrated in FIG. 6.

FIGS. 1-6 illustrate the effect varying levels of PX monomer and radiation intensity have on the compliance of the resulting pressure-sensitive adhesive.

EXAMPLES 21 TO 33

Medical Tapes

Representative uncrosslinked adhesive precursors of this invention prepared from about 98 wt.% IOA, about 2% AA and the amount of PX-A described in Table XI were coated on a woven cellulose acetate backing identical to that used to prepare Durapore TM brand medical tape available from 3M, which medical tape was used as a control. The effect of the intensity of radiation and amount of crosslinker on the compliance values and skin adhesion and residue values are shown in Table XI.

TABLE XI

| Examples | 21 | 22 | 23 | 24 | 25 | Control |
|---|---|---|---|---|---|---|
| wt. % PX-A | 0.05 | 0.05 | 0.075 | 0.075 | 0.075 | — |
| Radiation Intensity (mj/cm$^2$) | 0.066 | 0.265 | 0.033 | 0.066 | 0.265 | — |
| Compliance | 2.18 | 1.78 | 1.80 | 1.64 | 1.23 | — |
| T$_0$ (g/2.54 cm) | 49 | 29 | 55 | 43 | 28 | 46 |
| T$_{24}$ (g/2.54 cm) | 153 | 95 | 167 | 121 | 87 | 199 |
| Residue | 0 | 0 | 0 | 0 | 0 | 0.2 |

The procedures of Examples 21 to 25 were repeated with the exception that the polymer was composed of about 90 wt.% of IOA, 10 wt.% of NVP and the wt.% of PX-C shown in Table XIII.

TABLE XII

| Examples | 26 | 27 | 28 | 29 | 30 | 31 | 32 | 33 | Control |
|---|---|---|---|---|---|---|---|---|---|
| wt. % PX-C | 0.2 | 0.2 | 0.2 | 0.2 | 0.3 | 0.3 | 0.3 | 0.3 | none |
| Radiation Intensity (mj/cm$^2$) | 0.125 | 0.43 | 0.86 | 0.129 | 0.215 | 0.43 | 0.86 | 0.129 | none |
| Compliance | 2.40 | 1.73 | 1.20 | 1.20 | — | — | — | — | — |
| T$_0$ (g/2.52 cm) | 84 | 74 | 45 | 45 | 76 | 64 | 48 | 44 | 51 |
| T$_{24}$ (g/2.54 cm) | — | — | — | — | 84 | 75 | 61 | 54 | 205 |
| Residue | 0.1 | 0.2 | 0 | 0 | 0 | 0 | 0 | 0 | 0.6 |

The results shown in Tables XI and XII illustrate the superior skin adhesion values obtained with tapes using representative adhesives of this invention as compared with a commercially available medical tape as a control.

We claim:

1. An article comprising a support member having a surface, at least a portion of which surface is coated with a pressure-sensitive skin adhesive composition comprising a crosslinked copolymer comprised of A monomers and PX monomers, wherein:

A is a monomeric acrylate or methacrylate ester of a non-tertiary alcohol or a mixture of non-tertiary alcohols, said alcohols having from 1 to 14 carbon atoms with the average number of carbon atoms being about 4-12; and PX is a copolymerizable mono-ethylenically unsaturated aromatic ketone monomer free of ortho-aromatic hydroxyl groups and has the formula:

$$R-\overset{O}{\underset{\|}{C}}-\underset{(X)_n}{\bigcirc}-Y-Z$$

wherein
    R is lower alkyl or phenyl, provided that R may be optionally substituted with one or more halogen atoms, alkoxy groups or hydroxyl groups, further provided that when R is phenyl substituted with one or more hydroxyl groups, any such hydroxyl groups must be meta or para to the aromatic carboyl, X is halogen, alkoxy or hydroxyl, provided that when X is a hydroxyl group, that X must be meta or para to the aromatic carbonyl, n is an integer from 0 to 4, Y is a divalent linking group, and Z is an alkenyl group or an ethylenically unsaturated acyl group;

said PX monomer comprising from about 0.025% to about 0.5% by weight of said copolymer and the degree of polymerization of said copolymer being such that said copolymer has an inherent viscosity of from about 0.5 dl/g to about 1.4 dl/g before crosslinking, whereby upon crosslinking said copolymer by ultraviolet irradiation of said PX containing copolymer the skin adhesive composition has a creep compliance of from about $1.2 \times 10^{-5}$ cm$^2$/dyne to about $2.3 \times 10^{-5}$ cm$^2$/dyne when measured after about 3 minutes of subjection to stress.

2. An article in accordance with claim 1 wherein the support member is conformable.

3. An article in accordance with claim 2 wherein the support member is a conformable backing selected from the group consisting of synthetic films having a tensile modulus of less than about 400,000 psi and conformable fabrics.

4. An article in accordance with claim 1, wherein the support member has a moisture vapor permeability of at least about 500 g/m² when measured over about 24 hours at about 100° F. and under a humidity differential of about 80%.

5. A method of preparing an article comprising a support member having a surface, at least a portion of which surface is coated with a pressure-sensitive skin adhesive composition, said method comprising the steps of:

(a) preparing a precursor of said pressure-sensitive skin adhesive composition by copolymerizing A monomers and PX monomers wherein:

A is a monomeric acrylate or methacrylate ester of a non-tertiary alcohol or a mixture of non-tertiary alcohols, said alcohols having from 1 to 14 carbon atoms with the average number of carbon atoms being about 4–12; and PX is a copolymerizable mono-ethylenically unsaturated aromatic ketone monomer free of ortho-aromatic hydroxyl groups and has the formula:

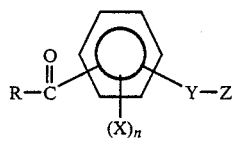

wherein

R is lower alkyl or phenyl, provided that R may be optionally substituted with one or more halogen atoms, alkoxy groups or hydroxyl groups, further provided that when R is phenyl substituted with one or more hydroxyl groups, any such hydroxyl groups must be meta or para to the aromatic carbonyl, X is halogen, alkoxy or hydroxyl, provided that when X is a hydroxyl group, that X must be meta or para to the aromatic carbonyl, n is an integer from 0 to 4, Y is a divalent linking group, and X is an alkenyl group or an ethylenically unsaturated acyl group; said PX monomer comprising from about 0.025% to about 0.5% by weight of the resultant copolymer and the degree of polymerization of said copolymer being such that said copolymer has an inherent viscosity of from about 0.5 dl/g to about 1.4 dl/g;

(b) coating at least a portion of the surface of said support member with said pressure-sensitive skin adhesive precursor; and (c) exposing said pressure-sensitive skin adhesive precursor to sufficient ultraviolet radiation to crosslink said precursor such that the resultant pressure-sensitive skin adhesive composition has a creep compliance of from about $1.2 \times 10^{-5}$ cm²/dyne to about $2.3 \times 10^{-5}$ cm²/dyne when measured after about 3 minutes of subjection to stress.

6. A method of adhering an adherend to a substrate comprising interposing between said adherend and said substrate an effective amount of an adhesive composition comprising a crosslinked copolymer comprised of A monomers and PX monomers, wherein:

A is a monomeric acrylate or methacrylate ester of a non-tertiary alcohol or a mixture of non-tertiary alcohols, said alcohols having from 1 to 14 carbon atoms with the average number of carbon atoms being about 4–12; and PX is a copolymerizable mono-ethylenically unsaturated aromatic ketone monomer free of ortho-aromatic hydroxyl groups and has the formula:

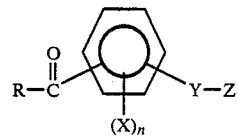

wherein

R is lower alkyl or phenyl, provided that R may be optionally substituted with one or more halogen atoms, alkoxy groups or hydroxyl groups, further provided that when R is phenyl substituted with one or more hydroxyl groups, any such hydroxyl groups must be meta or para to the aromatic carbonyl, X is halogen, alkoxy or hydroxyl, provided that when X is a hydroxyl group, that X must be meta or para to the aromatic carbonyl, n is an integer from 0 to 4, Y is a divalent linking group, and Z is an alkenyl group or an ethylenically unsaturated acyl group;

said PX monomer comprising from about 0.025% to about 0.5% by weight of said copolymer and the degree of polymerization of said copolymer being such that said copolymer has an inherent viscosity of from about 0.5 dl/g to about 1.4 dl/g before crosslinking, whereby upon crosslinking said copolymer by ultraviolet irradiation of said PX containing copolymer the adhesive composition has a creep compliance of from about $1.2 \times 10^{-5}$ cm²/dyne to about $2.3 \times 10^{-5}$ cm²/dyne when measured after about 3 minutes of subjection to stress.

7. A method in accordance with claim 6 wherein said adherend is a sheet material and said substrate is skin.

8. An article in accordance with claim 3 wherein the conformable backing has a moisture vapor permeability of at least about 500 g/m² when measured over about 24 hours at about 100° F. and under a humidity differential of about 80%.

9. An article in accordance with claim 3 wherein the conformable backing has a moisture vapor permeability of at least about 1000 g/m² when measured over about 24 hours at about 100° F. and under a humidity differential of about 80%.

10. An article in accordance with claim 9 wherein the conformable backing comprises a synthetic film having a tensile modulus of less than about 300,000 psi.

11. An article in accordance with claim 1 wherein Y is selected from the group consisting of a covalent bond, an oxygen atom, an amine group, an oxyalkyleneoxy group, and a carbamoylalkyleneoxy group.

12. An article in accordance with claim 1 wherein the copolymer is further comprised of a B monomer which is an ethylenically unsaturated compound copolymerizable with said A monomer, the amount by weight of B monomer being up to about 25% of the total weight of all monomers.

13. An article in accordance with claim 12 wherein the B monomer is selected from the group consisting of acrylic acid, methacrylic acid, itaconic acid, acrylamide, methacrylamide, acrylonitrile, methacrylonitrile, vinyl acetate, and N-vinylpyrrolidone.

14. An article in accordance with claim 12 wherein said A monomer is isooctyl acrylate, said PX monomer is paraacryloxybenzophenone, and said B monomer is acrylic acid.

15. An article in accordance with claim 1 wherein the degree of polymerization of said copolymer is such that said copolymer has an inherent viscosity of from about 0.55 dl/g to about 1.1 dl/g before crosslinking.

16. An article in accordance with claim 1 wherein R is phenyl.

17. An article in accordance with claim 1 wherein R is methyl.

18. An article in accordance with claim 1 wherein R is phenyl, n is zero such that $(X)_n$ is hydrogen, Y is oxygen, and Z is acryloyl, such that said PX monomer is paraacryloxybenzophenone.

19. A method in accordance with claim 5 wherein the degree of polymerization of said copolymer is such that said copolymer has an inherent viscosity of from about 0.55 dl/g to about 1.1 dl/g before crosslinking.

20. A method in accordance with claim 5 wherein R is phenyl, n is zero such that $(X)_n$ is hydrogen, Y is oxygen, and Z is acryloyl, such that said PX monomer is paraacryloxybenzophenone.

* * * * *